United States Patent [19]
Haynes et al.

[11] Patent Number: 5,972,659
[45] Date of Patent: Oct. 26, 1999

[54] MULTISPECIFIC ANTIGENIC PROTEINS

[75] Inventors: Joel Haynes, Memphis, Tenn.; Eric A. James, Willowdale; Robert T. Garvin, Toronto, both of Canada

[73] Assignee: Connaught Laboratories Limited, North York, Canada

[21] Appl. No.: 08/472,178

[22] Filed: Jun. 7, 1995

Related U.S. Application Data

[62] Division of application No. 08/187,135, Jan. 27, 1994, abandoned, which is a continuation of application No. 07/875,212, Apr. 28, 1992, abandoned, which is a continuation of application No. 07/530,457, May 30, 1990, abandoned, which is a continuation of application No. 07/134,376, Dec. 17, 1987, abandoned, which is a division of application No. 06/767,332, Aug. 21, 1985.

[30] Foreign Application Priority Data

Aug. 22, 1984 [GB] United Kingdom .................... 8421282

[51] Int. Cl.$^6$ ...................................................... C12P 21/04
[52] U.S. Cl. ...................... 435/69.7; 435/69.1; 435/69.3; 435/71.1; 435/71.2; 435/91.4; 435/91.42; 435/252.33; 435/320.1; 435/471; 935/25
[58] Field of Search ........................... 424/202.1, 196.11; 435/69.3, 70.1, 252.33, 320.1, 69.1, 69.7, 71.1, 71.2, 91.4, 91.42, 471; 935/25

[56] References Cited

U.S. PATENT DOCUMENTS 4,722,840  2/1988  Valenzu et al. ............................ 424/89
5,316,931  5/1994  Donson et al. .

FOREIGN PATENT DOCUMENTS 6553  12/1982  European Pat. Off. .

OTHER PUBLICATIONS

Maramorosch et al, *Methods in Virology*, vol. VII, Academic Press, N.Y. N.Y., 1984. pp. 265–266.
Collmer et al. Virology 126:449–458, 198.
Valenzuela et al (1982) Nature 298:347–50.
Boujes–Bocquet et al (1984) Md. Approaches Vaccine, ed. Chonoch et al Cold Spring Harbor, Abst.
Emini et al (1984) Virology 137:74–85.

*Primary Examiner*—Patricia A. Duffy
*Attorney, Agent, or Firm*—Sim & McBurney

[57] ABSTRACT

A novel conjugated protein produced by recombinant DNA techniques comprises a low molecular weight carrier protein portion that is normally self-aggregating to an immunogenic higher molecular weight proteinaceous material and a hapten portion wich is a peptide fraction that contains an epitope for an antigen for a pathogenic disease attached to the low molecular weight carrier portion. On aggregation of the self-aggregating protein, the hapten is on the surface of the viral particle, allowing for recognition of the hapten by the immune system. Upon introduction in vivo, the viral protein produces antibodies to both the self-aggregating protein and the hapten. A plurality of the conjugated proteins having different haptens can be combined into a viral protein to provide multi specific vaicines conferring immunity to a variety of pathogenic agents.

1 Claim, 11 Drawing Sheets

FIG. 1.

```
                  (5'..........................................      50
ATGTCTTACT   CGATTACCACTCCATCCCAGTTCGTTTTCCTGTCCTCTGC
TACAGAATGAGC    TAATGGTGAGGTAGGGTCAAGCAAAAGGACAGGAGACG

..................................................                  100
TTGGGCAGACCCGATCGAACTGATCAACCTGTGTACTAACGCACTGGGTA
AACCCGTCTGGGCTAGCTTGACTAGTTGGACACATGATTGCGTGACCCAT

..................................................                  150
ACCAGTTTCAGACTCAGCAGGCTCGTACTGTAGTTCAGCGTAAATTCTCT
TGGTCAAAGTCTGAGTCGTCCGAGCATGACATCAAGTCGCAGTTAAGAGA

..................................................                  200
GAAGTTTGGAAACCGTCTCCTCAGGTAACTGTTCGTTTCCCGGACTCTGA
CTTCAAACCTTTGGCAGAGGAGTCCATTGACAAGCAAAGGGCCTGAGACT

......5' ) ( 3'...................................                  250
CTTCAAAGT    ATACCGTTACAACGCTGTACTGGACCCGCTGGTTACCGCTC
GAAGTTTCATA    TGGCAATGTTGCGACATGACCTGGGCGACCAATGGCGAG

..................................................                  300
TGCTGGGCGCTTTCGACACTCGTAACCGTATCATCGAAGTAGAAAACCAG
ACGACCCGCGAAAGCTGTGAGCATTGGCATAGTAGCTTCATCTTTTGGTC

..................................................                  350
GCAAACCCGACCACCGCGGAAACTCTGGACGCAACCCGTCGTGTTGACGA
CGTTTGGGCTGGTGGCGCCTTTGAGACCTGCGTTGGGCAGCACAACTGCT

..................................................                  400
CGCTACCGTTGCAATCCGTTCCGCTATCAACAACCTGATCGTTGAACTGA
GCGATGGCAACGTTAGGCAAGGCGATAGTTGTTGGACTAGCAACTTGACT

..................................................                  450
TTCGTGGTACCGGTTCCTACAACCGCTCTTCTTTCGAATCTTCCTCCGGT
AAGCACCATGGCCAAGGATGTTGGCGAGAAGAAAGCTTAGAAGGAGGCCA

...................3' )                                             477
CTGGTATGGACCTCGGGCC    CGGCAACT
GACCATACCTGGAGC    CCGGGCCGTTGA
```

FIG. 6.
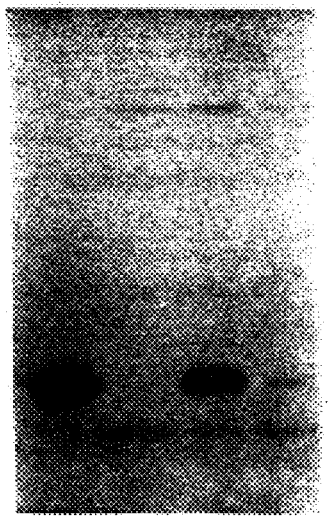
FIG. 7A.
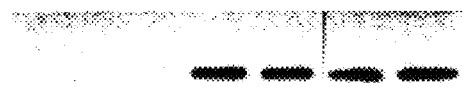
FIG. 7B.
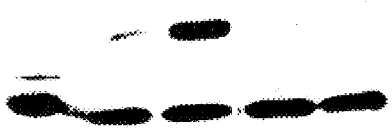

FIG.11A.1.
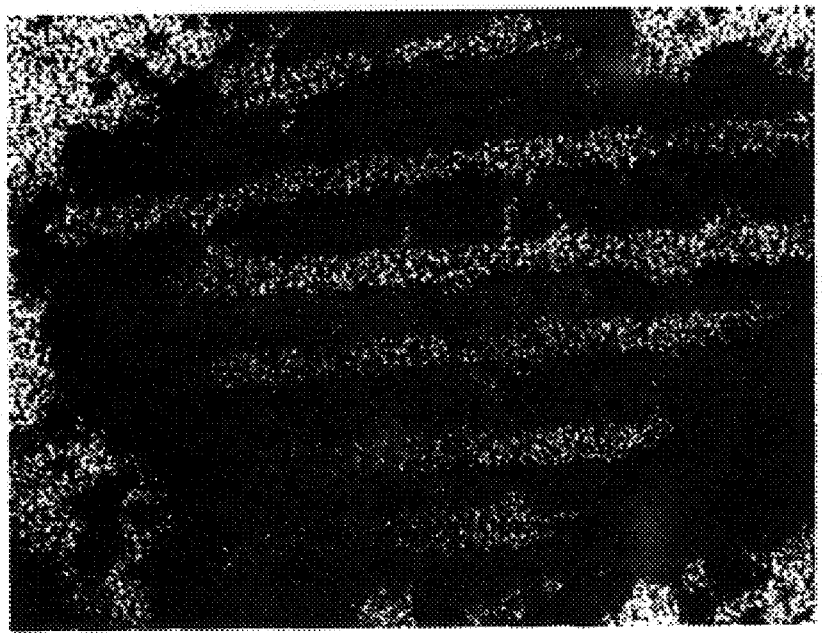
FIG.11A.2.
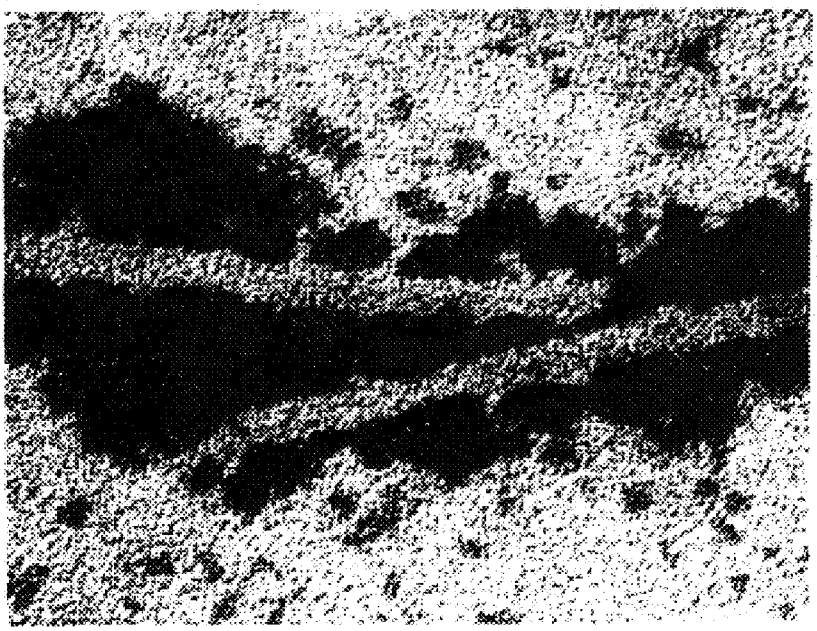

FIG.11B.1.
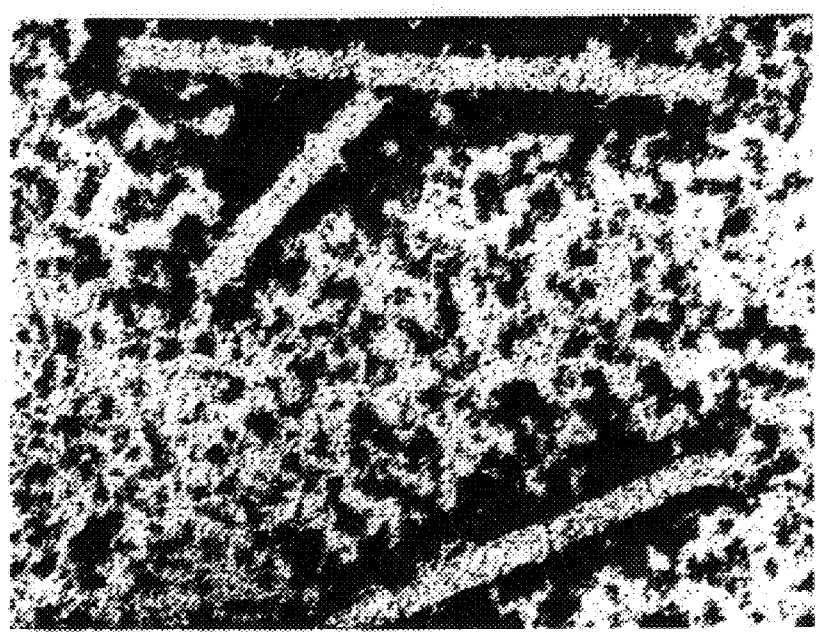
FIG.11B.2.
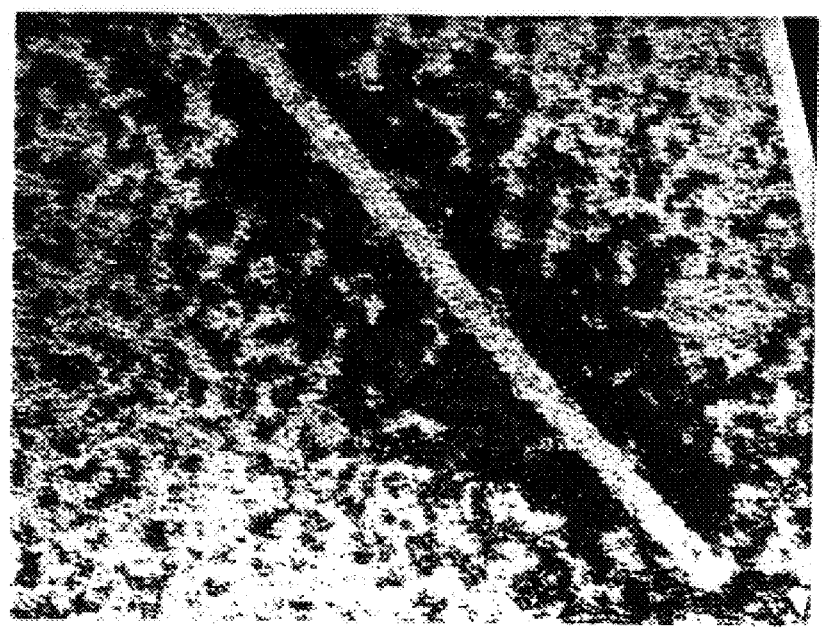

FIG.11C.1.
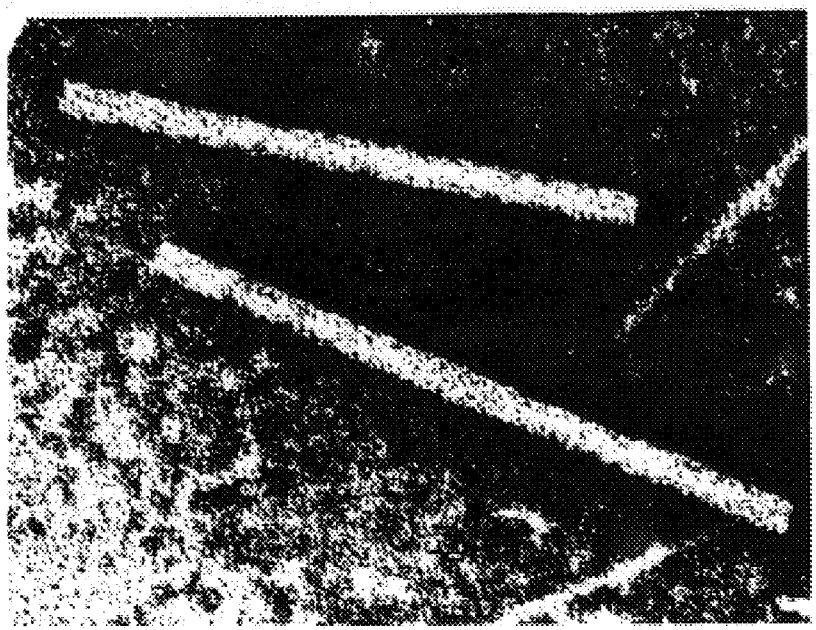
FIG.11C.2.
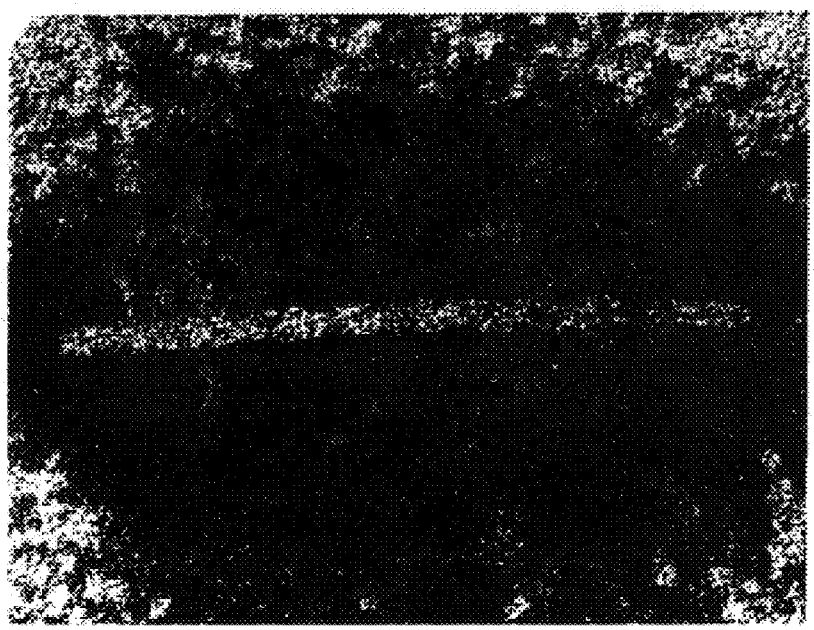

MULTISPECIFIC ANTIGENIC PROTEINS

This is a division of application Ser. No. 08/187,135 filed Jan. 27, 1994 now abandoned, which is a continuation of application Ser. No. 875,212 filed Apr. 28,1992 (now abandoned) which itself is a continuation of application Ser. No. 530,457 filed May 30, 1990 (now abandoned), which is a continuation of Ser. No. 07/134,376, filed Dec. 17, 1987 (abandoned) which is a division of Ser. No. 06/767,332 filed Aug. 29, 1985 (now abandoned).

FIELD OF INVENTION

The present invention relates to immunogenic proteins, their production by recombinant DNA techniques, their use as therapeutic agents and novel intermediate products.

BACKGROUND TO THE INVENTION

It is a known characteristic of a number of microorganisms, that they possess constituents which can be assembled in an orderly manner from one compound, often of low molecular weight, to provide a high molecular weight entity. These high molecular weight entities may take various forms, for example, as protein coats in the case of viruses, as pili in the case of certain bacteria and when the low molecular weight material is a carbohydrate the high molecular weight material can be the cell wall of a bacteria. This high molecular weight material is often highly immunogenic.

As an example of this assembly process, the Hepatitis B surface antigen is composed of a glycoprotein of molecular weight 29,000 Daltons, which on aggregation forms a particle containing 130 of the sub-units, having a molecular weight of $3.8 \times 10^6$ Daltons and known as the Dane particle. A similar situation occurs with Tobacco Mosaic Virus (hereinafter abbreviated to TMV) where a smaller protein aggregates in a single helix to form rods, containing large numbers of the smaller protein. Often, in the case of viruses, the sub-unit proteins can aggregate to their final polymeric form without the other constituents of the virus being present and under completely in vitro conditions.

It is also known that small molecules, which often act only poorly as immunogens in their ability to elicit antibodies in an in vivo system, when attached to a larger molecule that is itself antigenic, will give rise to improved antibody response to the smaller molecule, as well as the normal response to the larger carrier molecule. The small molecule attached to the larger in this system, is called a hapten, and can vary in size from small to quite large. In one example of this combination, of interest to the health care field, a small portion of the Hepatitis B surface antigen, comprising a sequence of fifteen amino acids, which is not itself antigenic, has been covalently bound to the antigenic protein, keyhole limpet hemocyanin, and the resulting conjugate elicited antibodies in an in vivo system that cross-reacted with the native surface antigen and also with the whole hepatitis virus. This system of carrier-hapten could be the basis for an effective vaccine against a disease for which the hapten codes.

In a modification of this general idea as disclosed in U.S. Pat. No. 4,496,538 a carrier hapten vaccine may comprise a hapten which is a carbohydrate from a known pathogenic organism, Haemophilus influenzae b, and a carrier which is diphtheria toxoid. It has been shown that this carrier hapten is not only immunogenic but will protect against the disease.

Recombinant DNA techniques have been used to produce fairly large quantities of proteins in microorganisms, that are normally foreign to the organism. Such techniques involve inserting into the organism a vector containing DNA coding for the desired foreign protein. In this way it is possible for the organism to produce not only foreign proteins, but also proteins that differ from the naturally occurring ones by having either changed amino acid sequences, additions or subtractions. The gene coding for these foreign proteins may be isolated from a natural source, may be synthesized, and may be altered using restriction enzymes to obtain the gene for a changed protein.

Such recombinant DNA techniques, applied to the formation of viral proteins, permit the preparation of proteins, which can be used as vaccines, which would contain none of the contaminants associated with present viral vaccines produced by standard methods, where the virus is grown on a cell substrate and the final vaccine can contain products from the cell substrate, the medium and nucleic acid from the virus, all of which can have deleterious effects.

SUMMARY OF INVENTION

In the present invention, there are provided certain novel protein materials, as described below, which are conveniently produced by recombinant DNA techniques, which are useful in providing multivalent immunogenic vaccines, and which employ the carrier-hapten concept described above.

In accordance with one embodiment of the invention, there is provided a conjugated protein comprising a low molecular weight carrier protein portion that is normally self-aggregating to an immunogenic higher molecular weight proteinaceous material and a hapten portion which is a peptide fraction which represents an epitope for an antigen for a pathogenic disease attached to the low molecular weight carrier portion. The manner of attachment of the hapten to the carrier protein should be such that the self-aggregation property of the carrier protein is not impaired and also such that, on aggregation of the self-aggregating protein, the hapten is on the surface of the assembled particle, allowing for recognition of the hapten by the immune system.

The combination of the self-aggregating protein and hapten when aggregated into a high molecular weight structure and introduced in vivo produces antibodies to the self-aggregating protein and also to the hapten, so that there results protection against the disease for which the epitope codes as well as an immunogenic response to the self-aggregating protein.

One significant, advantageous and novel feature of the invention is that the aggregated proteins may be prepared with different haptens joined to the self-aggregating protein, so that when the protein aggregates, the resultant proteinaceous particles possess a number of different epitopes on the surface. When these viral particles are used in vivo, antibodies to all the haptens are elicited, thereby providing protection against the various diseases for which there are haptens present. In this way, there may be provided a single vaccination against a multiplicity of diseases by the preparation and use of a single active proteinaceous material.

The conjugated proteins of this invention are conveniently prepared by inserting a synthetic gene into a vector by recombinant DNA techniques, introducing this recombinant vector into an organism, growing the organism, isolating the protein-hapten conjugate and allowing the conjugate to aggregate.

The present invention involves fundamental and new concepts which are applicable to any self-aggregating protein and to any hapten. The invention will be particularly described hereinafter for the specific case of the self-aggregating protein being the coat protein of tobacco mosaic virus and the haptens that contain epitopes for polio viruses Types 1 and 3, but it will be apparent that the techniques and procedures are readily applicable to a wide range of other self-aggregating proteins, such as capsid, coat and other proteins from prokaryotic and eukaryotic plant and animal viruses, including the Hepatitis B surface antigen, in addition to numerous non-viral proteins such as prokaryotic pilins, flagellins and ribosomal proteins and eukaryotic tubulins, muscle filaments and ribosomal proteins. It will also be apparent that the techniques and procedures are readily applicable to a wide range of other haptens from such viral pathogens as adenoviruses, herpesviruses, poxviruses, picornaviruses, hepatitis viruses and a variety of tumour viruses. In addition bacterial pathogens such as pneumococci and streptococci and others could be used.

BRIEF DESCRIPTION OF DRAWINGS

FIG. 1 illustrates the nucelotide sequence for the TMV coat protein gene;

FIG. 6 is a Western Blot of TMV coat protein recovered from E.coli containing plasmid pTMV-6;

FIGS. 7A and 7B are a Western Blot of TMV coat protein and TMV-polio 3 conjugate protein from E.coli containing pTMV-6 and pTMV-polio 3;

FIGS. 11A.1, 11A.2, 11B.1, 11B.2, 11C.1 and 11C.2 show electron micrographs of aggregated TMV-Polio 3, coaggregated TMV-Polio 3 and TMV-Polio 1 and aggregated TMV-Polio 12 after 2 treatment with anti-type 3 antibody.

DESCRIPTION OF PREFERRED EMBODIMENTS

In the utilization of the present invention to effect the vaccination of mammals against a multiplicity of diseases, the following are the preferred methods to achieve the desired results for the specific case referred to above.

Figure 2:
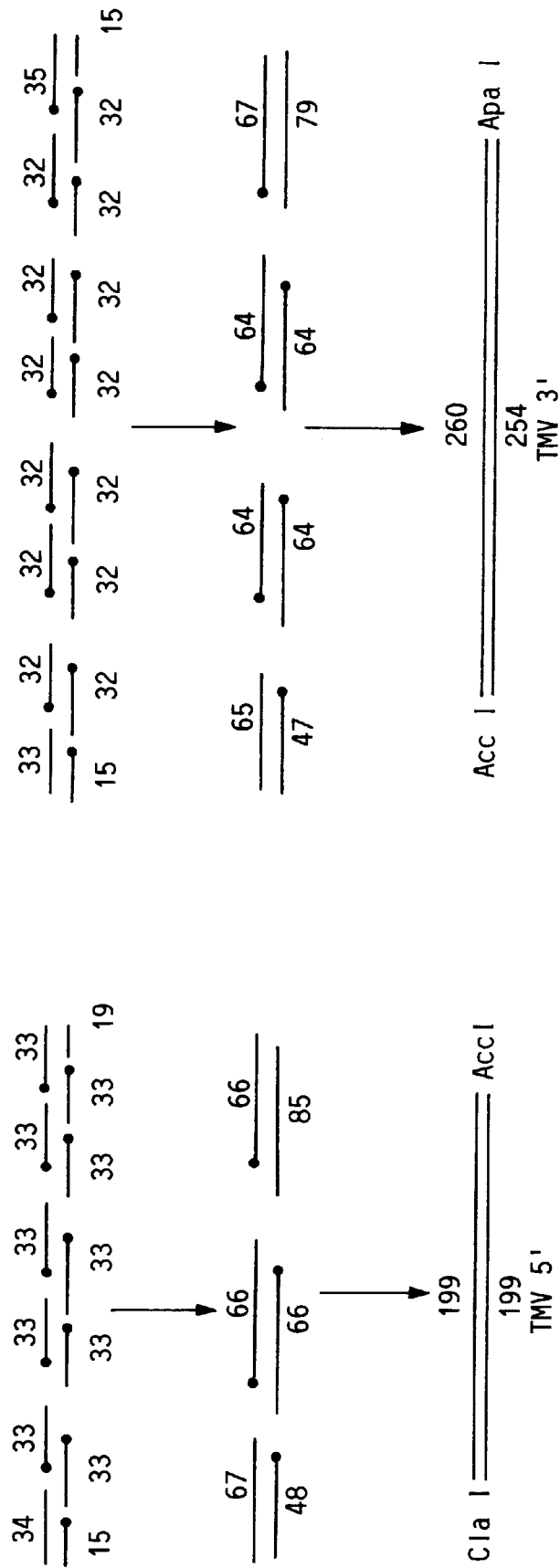
FIG. 2 illustrates schematically the procedure of formation of the nucleotide sequences TMV5' and TMV3'.

Two synthetic DNA fragments, each coding for approximately half of the TMV coat protein, are both assembled from a collection of single stranded DNA oligonucleotide fragments produced on an automated DNA synthesizer. The nucleotide sequence of the synthetic TMV coat protein gene is shown in FIG. 1. This DNA sequence codes for the authentic amino acid sequence reported [Proc.Nat.Sci.,USA, 1982,vol.79,pp5818–5822] for the coat protein of the vulgare strain of TMV. The synthetic sequence, however, is different from the natural gene sequence as preferential prokaryotic codons are chosen for most of the coding positions. The region of the sequence of FIG. 1 marked "5'" which consists of 199 base pairs in the top strand and 199 base pairs in the bottom strand may be assembled from a collection of 13 single stranded DNA oligonucleotides, as shown in FIG. 2 and inserted into a modified linearized pBR322 plasmid containing Cla I and Acc I restriction ends. Propagation of this recombinant plasmid in E.coli and its subsequent cleavage with Cla I and Acc I restriction endonucleases permits the production of unlimited quantities of the "5'" TMV coat protein gene fragment.

The region marked "3'" in FIG. 1 which consists of 260 base pairs in the bottom strand may be assembled from a collection of 17 single stranded DNA oligonucleotides as shown in FIG. 2 and inserted into a modified pBR322 linearized plasmid containing Acc I and Apa I restriction ends. In this case the EcoR1 site of pBR322 was converted onto an ApaI site by insertion of a synthetic DNA linker at the EcoR1 site. Cleavage of this modified plasmid with AccI and APaI results in a linear fragment to which can be ligated a synthetic Acc I-Apa I fragment for propagation in E.coli. Propagation of this recombinant plasmid in E.coli permits the production of unlimited quantities of the "3'" TMV coat protein gene fragment.

Figure 3:
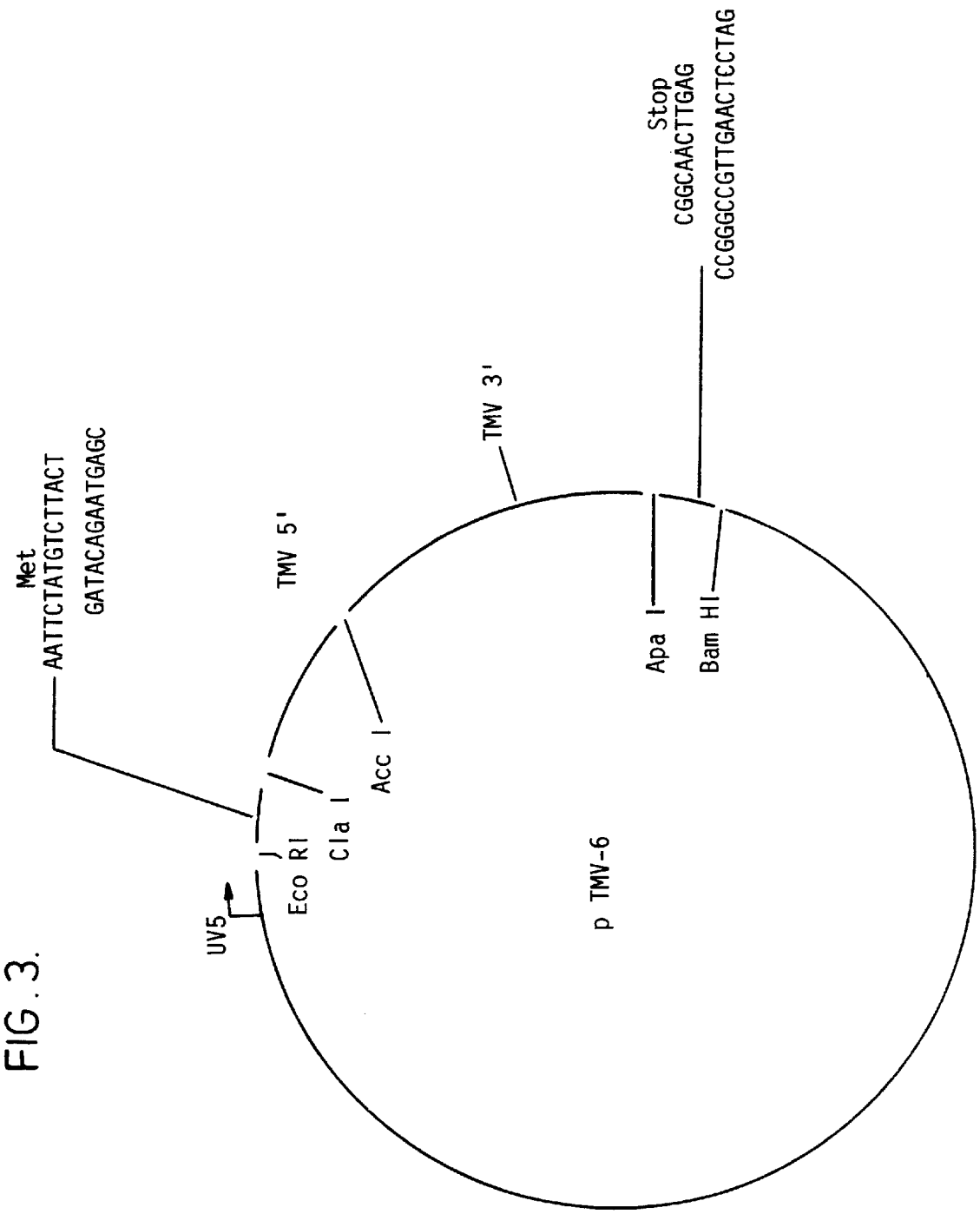
FIG. 3 depicts plasmid pTMV-6, with the major restriction sites and constitution of the synthetic recombinant TMV gene being shown.

The complete TMV coat protein gene is constructed from the TMV 5' and the TMV 3' fragments plus two additional synthetic double stranded DNA fragments and a pBR322 linearized plasmid vector fragment containing the lac UV5 transcriptional promoter. The resultant plasmid is illustrated in FIG. 3, which shows a pBR322 plasmid containing the E.coli lac UV5 transcriptional promoter which has been linearized and contains Eco RI and Bam HI restriction ends. The TMV5' and TMV3' fragments are ligated to each other and also to the EcoR1 and BamHI ends of the pBR322 plasmid by virtue of the synthetic double stranded DNA linkers. The novel recombinant plasmid, illustrated in FIG. 3, is designated pTMV-6 and contains a complete TMV coat protein coding sequence under the control of the bacterial lac UV5 promoter. The transcription initiation site for the lacUV5 promoter lies approximately 37 nucleotides from the EcoR1 end such that insertion of the TMV gene between the EcoR1 and BamHI sites results in efficient mRNA transcription of the gene.

The plasmid pTMV-6, constructed as described above, may be cloned in any convenient organism, for example, E.coli strain HB101, before being purified. Conveniently the purified plasmid is transfected into E.coli strain JM103, since this strain overproduces the lac repressor protein which serves to maintain the TMV gene in a transcriptionally inactive state until an inducer is added.

The recombinant TMV coat protein, synthesized in bacteria containing the pTMV-6 plasmid, may be separated from the bacteria and purified by a technique which takes advantage of the self assembling properties of the protein under acidic conditions. After culturing, the cells may be lysed by sonication and then dialysed against an acidic buffer. Under these conditions, a significant portion of the bacterial proteins become insoluble and subsequently may be readily removed by centrifugation. The acidic conditions are sufficient to induce the TMV coat protein to polymerize into a high molecular weight helix structure such that its molecular weight is larger than any preexisting bacterial protein in the solution and hence can be easily purified by chromatographic techniques.

Figure 4:
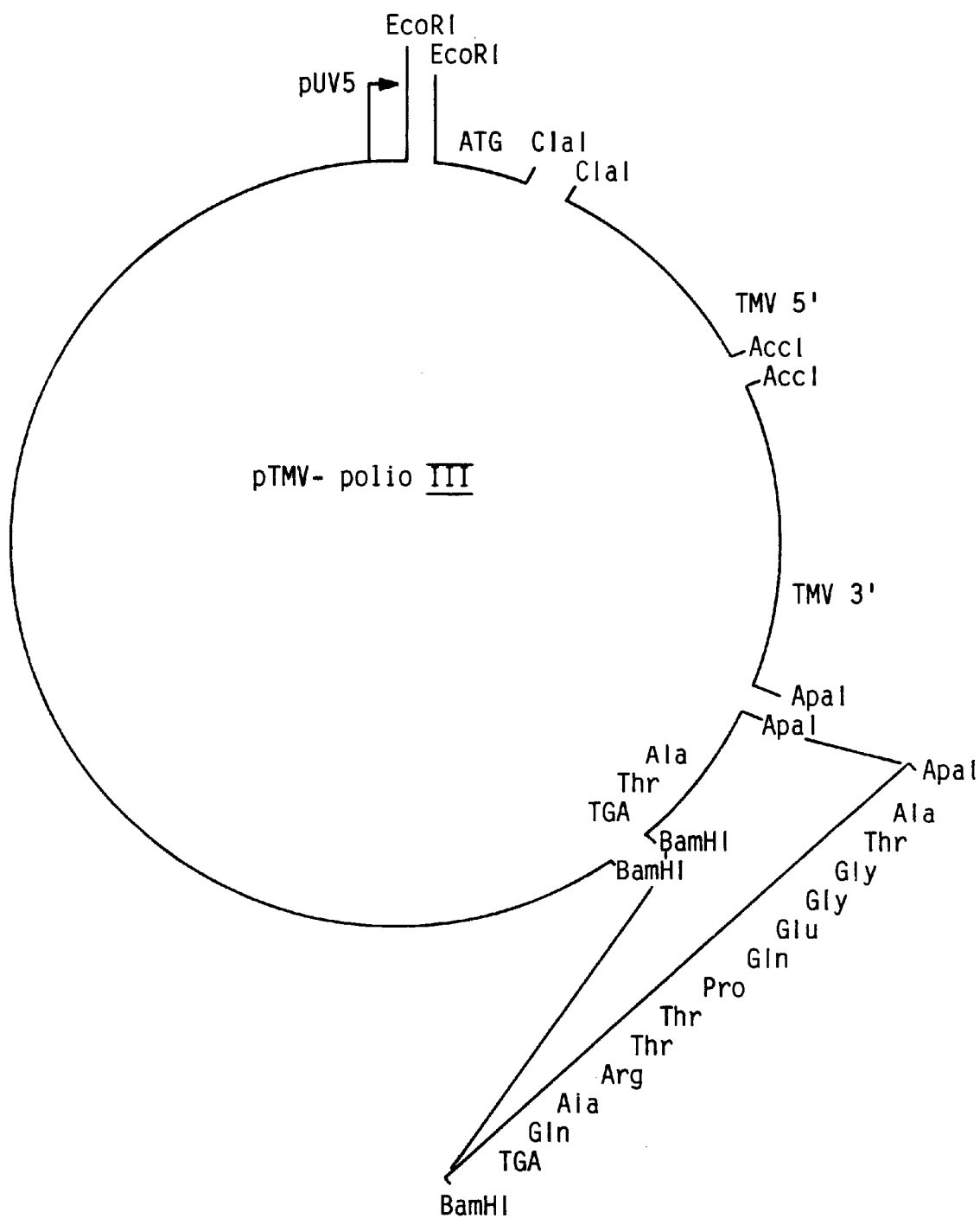
FIG. 4 depicts plasmid pTMV-polio 3, with the amino acid sequence for the polio 3 epitope being detailed.

The pTMV-6 plasmid contains an Apa I restriction site preceding the translation termination codon and a Bam HI site following the codon. This allows the termination codon region to be excised from the plasmid and replaced with a modified region to provide a modified plasmid coding for a conjugate protein. In one embodiment, this region may be replaced with a DNA fragment coding for the authentic end of the TMV coat protein plus a 10 amino acid extension. The first two amino acids of this extension are glycine and serve as a spacer region while the last eight amino acids comprise a specific neutralization epitope from the VP1 protein of polio virus type 3. This epitope has previously been shown [Nature,1983,Vol.304,pp 459–462] to represent a major neutralization epitope from polio type 3, so attachment of this epitope to the C-terminus of the TMV coat protein and subsequent polymerization of the hybrid coat protein produces an effective vehicle for presentation of this epitope to the immune system. The modified novel plasmid is illustrated in FIG. 4 and is designated pTMV-polio 3.

The TMV-Polio 3 conjugate, after expression from the organism, may be separated and purified in an identical manner to that described above for the TMV protein.

Figure 5:
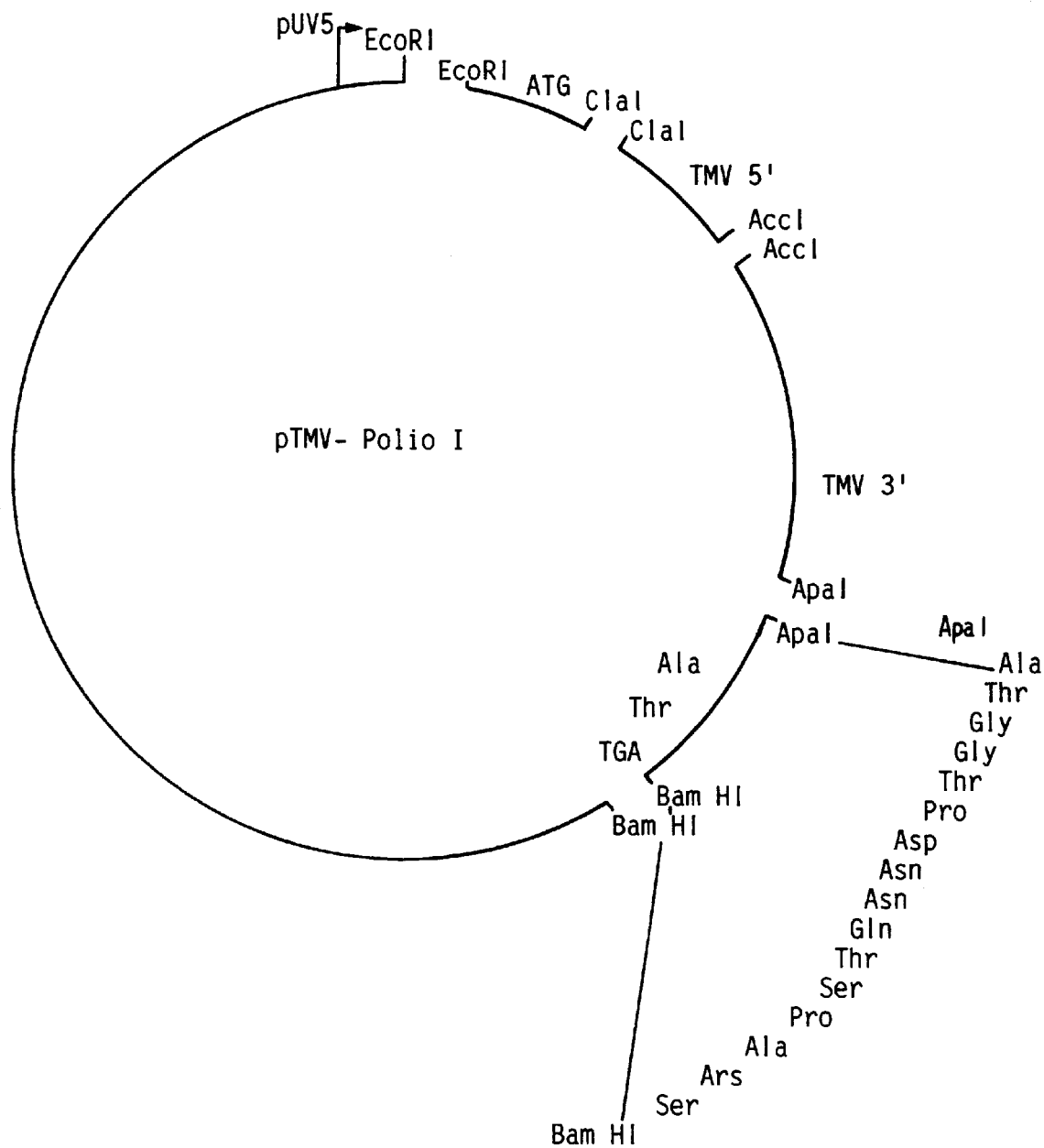
FIG. 5 depicts plasmid pTMV-polio 1, with the amino acid sequence for the polio 1 epitope being detailed.

In another embodiment, the pTMV-6 expression plasmid may be modified by removing the Apa I-Bam HI fragment and replacing it with a DNA fragment coding for the last two amino acids of the TMV coat protein C-terminus plus two glycines serving as a spacer and 11 additional amino acids representing a polio type 1 antigenic epitope. FIG. 5 shows the structure of the novel modified plasmid which is designated pTMV-polio I and the sequence of the new epitope. The type 1 epitope is located on the VP2 protein of Polio type 1 [J.Virol.1984,vol 52,pp 719–721] and has been described as a neutralisation epitope. The sequence of the 12 amino acid epitope was originally reported as: Thr-Pro-Asp-Asn-Asn-Gln-Thr-Ser-Pro-Ala-Arg-Arg. The sequence reported here differs in the last amino acid position in which the Arg is changed to Ser to be in complete agreement with the reported amino acid sequence of Mahoney strain of Polio type 1 [Nature, 1981,vol 291,pp 547–553]. The TMV-polio I product can be isolated from extracts of *E.coli* in an identical fashion to the TMV-polio 3 product as described above.

An important feature of the present invention, as noted earlier, is the ability to construct an aggregated molecule of TMV coat protein-like subunits in which the individual subunits making up the aggregated molecule may contain more than one type of antigenic epitope. As an example, a mixture of TMV-polio 1 and TMV-polio 3 may be formed and the subunits copolymerized into helix structure in which individual helix molecules would contain both epitopes by aggregation of the TMV-protein moieties. The ability to prepare such multi specific epitope products permits the production of multi specific vaccines conferring immunity to a variety of pathogenic agents.

EXAMPLE 1

This Example illustrates the assembly and formation of the TMV 5' fragment.

The TMV 5' fragment was assembled from a collection of 13 oligonucleotides in a two stage anealing and ligation strategy as shown in FIG. 2. The oligonucleotides were divided into three groups of four, four, and five oligonucleotides respectively for subsequent anealing and ligation reactions. Prior to annealing each DNA was phosphorylated on its 5' end except for the 34-mer of group I and the 19-mer of group III. This prevented the group I and the group III double stranded ligation products from forming head to head dimers as a result of ligation of the palindromic restriction ends to one another. The double stranded products of each of the three anealing and ligation reactions were purified by polyacrylamide gel electrophoresis. The position of each product within the purification gel was easily determined as the oligonucleotides were rendered radioactive during the phosphorylation reaction by use of a radioactive substrate. The purified products from the group I, II, and III ligations were anealed to one another for the second stage ligation reaction. The final product, consisting of a double stranded DNA molecule (199 base pairs in each strand) was purified by polyacrylamide gel electrophoresis and ligated into a pBR322 linearized plasmid containing Cla I and Acc I restriction ends for propagation in bacteria. The recombinant plasmid was propagated in *E.coli* [strain HB101] for production of the TMV 5' fragment.

EXAMPLE 2

This Example illustrates the assembly and formation of the TMV 3' fragment.

The 3' fragment of the TMV coding sequence was assembled from a collection of 17 oligonucleotides as shown in FIG. 2. The oligonucleotides were divided into four groups of four, four, four, and five oligonucleotides respectively. All oligonucleotides were phosphorylated using a radioactive ATP except the 33-mer of group I and the 15-mer of group IV. As in Example 1, this was to prevent dimerization of the group I and group IV ligation products due to the palindromic restriction ends. The four groups were anealed and ligated and the subsequent ligation products were purified by denaturing polyacrylamide gel electrophoresis. The use of denaturing gels resulted in the ligation products migrating as single stranded molecules. It was found that denaturing gels demonstrated a higher degree of resolution and abolished the appearance of unidentifiable bands which sometimes occurred during native gel electrophoresis as a result of nonspecific association between various oligonucleotides.

The two single stranded products of each of the four ligation reactions were purified from the denaturing gel and anealed together for the second stage ligation reaction. Following ligation, the product, consisting of a 260 base pair top strand and a 254 base pair bottom strand was purified from a denaturing polyacrylamide gel. Following anealing of the two strands, the resultant double stranded DNA was inserted into a linearized pBR322 plasmid containing Acc I and an Apa I restriction ends. The recombinant plasmid was propagated in *E.coli* [strain HB101] for production of the TMV 3' fragment.

EXAMPLE 3

This Example illustrates the formation of the complete TMV coding sequence and the formation of pTMV-6.

The TMV coat protein expression plasmid was prepared by a five-way ligation reaction in which the TMV 5' and the TMV 3' fragments were ligated to one another by their common Acc I restriction ends and the resultant 450 base pair fragment was ligated to the the pBR322 vector with the aid of two short, double stranded linker fragments (FIG. 3.). One linker fragment connected the Eco RI end of the pBR322 plasmid to the Cla I end of the TMV fragment while the other linker connected the Bam HI end of the plasmid to the Apa I end of the TMV fragment. In addition to performing a connecting function during the ligation, the linker DNAs also supplied the remaining codons and the translational start and stop signals to complete the TMV coding sequence (see FIG. 1). The resulting plasmid pTMV-6 is illustrated in FIG. 3.

EXAMPLE 4

This example illustrates the expression of the TMV coat protein.

The pTMV-6 plasmid prepared as described in Example 3 after cloning in *E.coli* strain HB101 was purified and transfected into *E.coli* strain JM103 using standard methods. Expression of the TMV gene in the bacteria was induced with 1 mM Isopropyl B-D-Thiogalactopyranoside [IPTG]. A 0.5 ml sample of the culture was taken, the bacteria centrifuged and lysed by SDS treatment at 100° C. This whole cell extract was electrophoresed on an SDS polyacrylamide gel after which the individual proteins were blotted to nitrocellulose paper and the presence or absence of TMV like material determined using anti-TMV antibodies (see FIG. 6): FIG. 6 shows the results of this experiment in which the bacteria containing only the plasmid pBR322 fail to show a positive signal migrating in the TMV coat protein position. However, bacteria containing the synthetic coat protein gene show a positive band migrating in exactly the same position as the authentic TMV coat protein marker obtained from the actual virus.

EXAMPLE 5

This Example illustrates the recovery of TMV protein from cell cultures.

Figure 8:
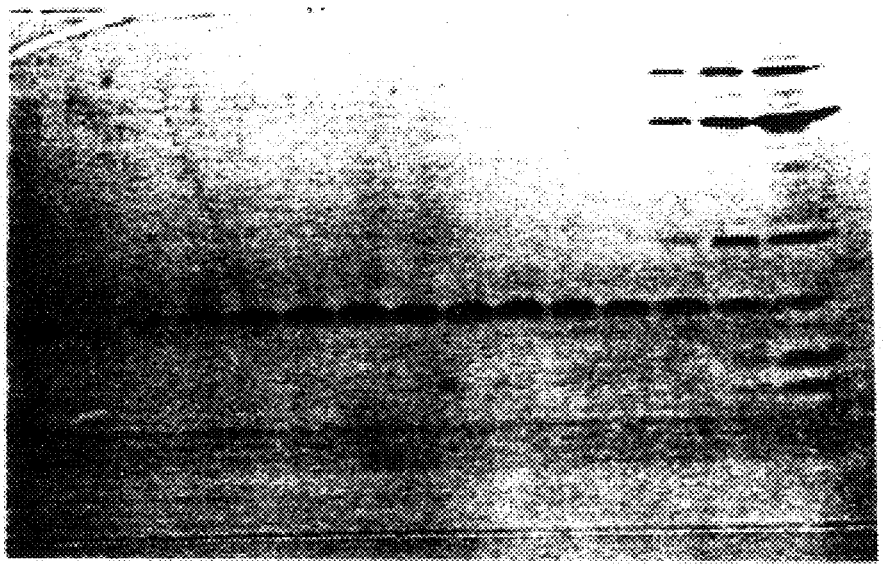
FIG. 8 is an SDS-polyacrylamide gel electrophoresis of fractions eluted from a chromatographic column containing TMV coat protein.

Bacteria (*E.coli* strain JM103) harbouring the pTMV-6 recombinant plasmid prepared as described in Example 3 were cultured in the presence of IPTG to induce expression from the lacuv5 promoter and cells were harvested by centrifugation. Bacteria were resuspended in sonication buffer and lysed by sonication after which cellular debris was removed by low speed centrifugation. The supernatant was dialyzed against a pH 5.0 buffer consisting of 0.1 M sodium acetate overnight at room temperature. Therefore, the sample was applied to a Sepharose 6B column and the the resultant peaks were analyzed by polyacrylamide gel electrophoresis (see FIG. 8) which demonstrated the void fractions to contain a single product migrating in the exact position as the authentic coat protein marker from TMV virus. Control experiments in which bacteria lacking the TMV expression plasmid were processed in an identical manner showed no detectable product in the void fractions.

EXAMPLE 6

This Example illustrates the formation of pTMV-Polio 3.

The preparation of a gene coding for an altered TMV coat protein containing an antigenic epitope at its C-terminus was accomplished by cleaving the pTMV-6 plasmid (FIG. 3) with Apa I and Bam HI and removing the small fragment coding for the C-terminus of the coat protein. This fragment was replaced with another synthetic DNA fragment coding for the coat protein C-terminus plus two glycine residues and an additional eight amino acids representing a dominant antigenic epitope from the VP1 protein for polio type 3. The resulting plasmid is shown in FIG. 4.

EXAMPLE 7

This Example illustrates the expression of the TMV-Polio 3 conjugate protein.

Bacterial cultures of *E.coli* strain JM103 containing either the pTMV-6 plasmid prepared as described in Example 3 or the pTMV-polio 3 plasmid as described in Example 6 were induced to express with IPTG. 0.5 ml of each culture was harvested by centrifugation and the bacterial pellets were lysed with SDS at 100° C. The whole cell extracts were electrophoresed on an SDS polyacrylamide gel after which the proteins were blotted to nitrocellulose and challenged with anti TMV and anti polio type 3 antibodies. FIG. 7 shows the results of this experiment in which the anti TMV antibody reacted with a product from the PTMV-6 containing bacteria which comigrates with the authentic TMV coat protein marker. The anti TMV antibody also reacted with a TMV like product from the pTMV-polio 3 containing bacteria but this material displays a reduced mobility relative to the TMV marker. This was the expected result as the TMV-polio 3 product contains an additional 10 amino acids at it C-terminus and should be expected to migrate differently.

Reaction of the blot with the anti-polio type 3 antibody resulted in a positive signal from the TMV-Polio 3 product while the unmodified TMV failed to react.

EXAMPLE 8

This Example illustrates the recovery of the TMV-Polio 3 conjugate protein from cell cultures.

Figure 9:
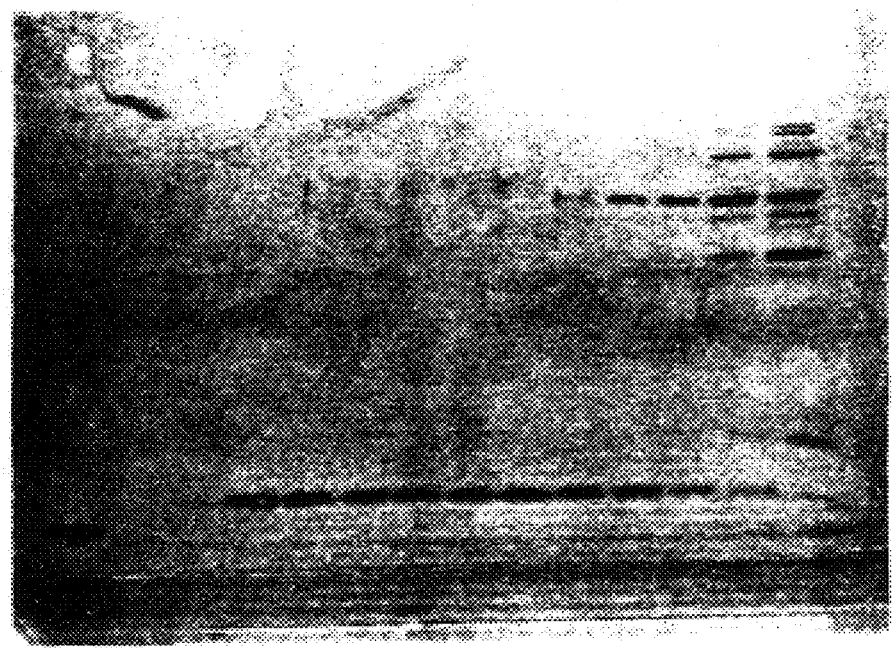
FIG. 9 is an SDS-polyacrylamide gel electrophoresis of fractions eluted from a chromatographic column containing TMV-polio 3 conjugate protein.

Purification experiments for TMV-polio 3 were performed in an identical manner to that already described in Example 3 for TMV in which bacteria were cultured in the presence of IPTG, harvested, and lysed by sonication. After removal of cell debris by centrifugation the supernatant was dialyzed against a pH 5.0 buffer to stimulate aggregation of the TMV-polio 3 product. Sepharose 6B chromatography resulted in a small void peak containing only a single product which migrated slightly slower than the authentic TMV coat protein marker in SDS polyacrylamide gels (see FIG. 9). The fact that the TMV-polio 3 behaves similarly to the TMV coat protein during the purification process indicates that the presence of the C-terminal extension does not interfere with the acid pH induced aggregation of the coat protein product. Moreover, the type 3 epitope actually may enhance the polymerization as the void peak from TMV-polio 3 purifications is reproducibly ahead of the void peak from TMV purifiactions suggesting that the former has aggregated to a higher molecular weight under these conditions.

EXAMPLE 9

This Example illustrates electron microscopic analysis of the TMV protein and the TMV-Polio 3 conjugate.

Figure 10A:
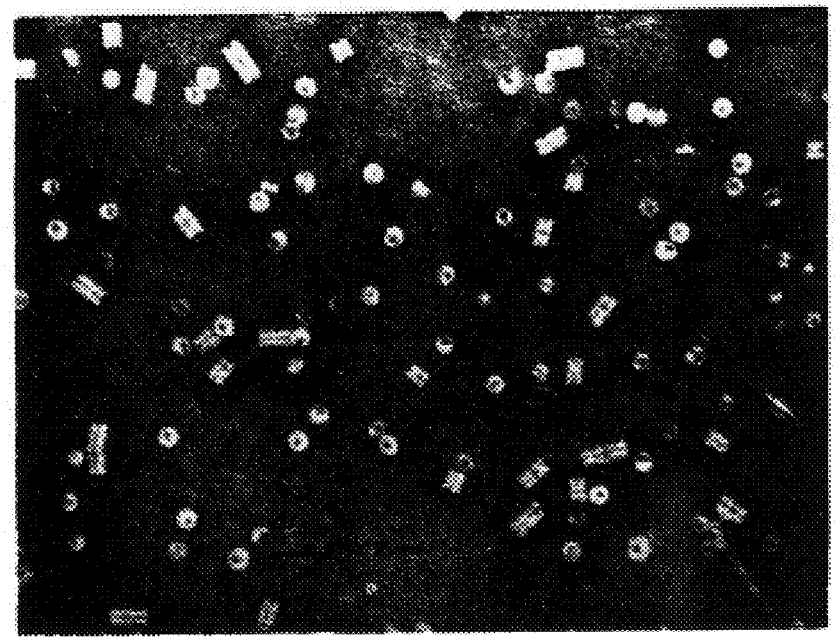
FIGS. 10A and 10B show electron micrographs of aggregated TMV coat protein and aggregated TMV-polio 3 conjugate protein, respectively.
Figure 10B:
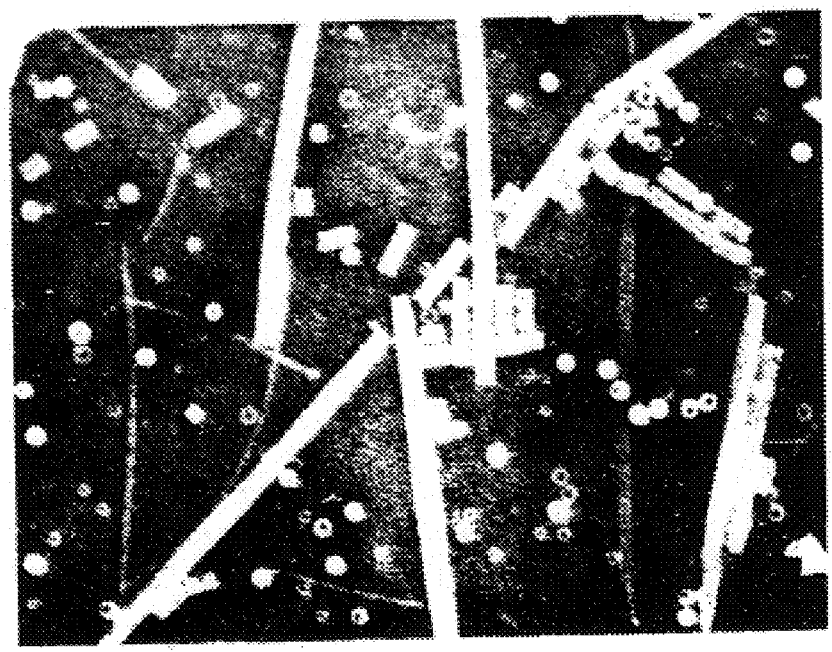

Electron microscopic analysis was performed on pH 5.0 samples of TMV and TMV-Polio 3, produced as described in Examples 5 and 8 respectively, in order to show that the aggregation seen at this pH represented an authentic TMV type of polymerisation reaction. Samples of both the *E. coli* produced TMV coat protein and TMV-polio 3 were purified from pH 5.0 *E. coli* extracts by Sepharose 6B chromatography as described in the above Examples 5 and 8. These samples were subjected to negative staining techniques and observed under the electron microscope. As may be seen from FIG. 10 both samples demonstrated the presence of short rods and disk type structures typical of the authentic TMV coat protein under acid conditions. Moreover, the TMV-Polio 3 sample (FIG. 10B) demonstrated the presence of long rods suggesting that it aggregated more efficiently than the unmodified TMV product.

EXAMPLE 10

This Example illustrates the reversibility of the aggregation of the TMV protein.

An important feature of the polymerization reaction displayed by the authentic TMV coat protein is its reversibility.

A sample of TMV-polio 3 isolated from the void fractions from a pH 5.0 Sepharose 6B column, as described in Example 8, was dialyzed against 0.1 M Tris pH 8.0 at 4° C. and chromatographed once again on Sepharose 6B. The mobility of the product decreased such that the TMV-polio 3 was found only in the inclusion fractions. Moreover, a second shift back to pH 5.0 by dialysis against 0.1 M sodium acetate resulted in yet another mobility shift in which the material was again found in the void fractions following gel filtration chromatography.

EXAMPLE 11

This Example shows the result of immunisation experiments.

An initial immunization experiment was set up in which the TMV coat protein and TMV-polio 3 conjugate protein, produced as described in Examples 5 and 8 respectively, were injected into rats via an intradermal (ID) and intraperitoneal (IP) route. Each rat received either 100 ug TMV ID and 100 ug TMV IP or 100 ug TMV-polio 3 ID and 100 ug TMV-polio 3 IP. All injections were with complete Freund's adjuvant and each rat received a total of four injections. The first and second injections were three weeks apart while the remaining injections were two weeks apart. The results are set forth in the following Table I.

TABLE I

| INOCULUM | RAT | LOG GEOMETRIC MEAN TITERS | | |
|---|---|---|---|---|
| | | 1 week after 3rd injection | 1 week after 4th injection | 3 weeks after 4th injection |
| TMV-polio | 1 | 6 | 7 | 9 |
| 3 | 2 | 3 | 2 | 9 |
| TMV | 3 | 0 | 0 | 0 |
| | 4 | 0 | 0 | 0 |

As may be seen from these results, the rats which received the TMV-polio 3 product produced anti polio neutralizing antibodies. Titers are expressed as a log2 geometric mean. Virus particle neutralization was confirmed by plating virus treated with serial dilutions of antisera from individual test rats on tissue culture cells. The absence of cytopathic effects indicated complete neutralization of all virus particles.

A second immunization experiment was established in order to compare the immune response to three different forms of the TMV-polio 3 product, which were: pH 5.0 aggregated TMV-polio 3 (Example 8), pH 8.0 dissaggregated TMV-polio 3 (Example 10), and RNA assembled TMV-polio 3. The latter product, the RNA assembled material, represented a preparation of TMV-polio 3 which had been incubated in vitro with authentic TMV genomic RNA. Such a reaction resulted in the formation of pH stable virus like particles consisting of TMV-polio 3 and TMV RNA. Such products were very similar to authentic TMV virus as shown by electron microscopic observation. The RNA assembled TMV-Polio 3 demonstrated heterogeneity in rod length attributable to RNA degradation prior to assembling.

This RNA assembled preparation of TMV-polio 3 served as a control in the immunization study. It was reasoned that if the immune response to the pH 5.0 aggregated TMV-polio 3 was more similar to the response to the RNA assembled product than to the pH 8.0 dissaggregated material, then this would indicate that the pH 5.0 product was remaining largely in a high molecular weight form during induction of the immune response. On the other hand, if the pH 5.0 TMV-polio 3 response was more similar to the pH 8.0 response then it could be reasoned that the pH 5.0 material was dissaggregating soon after injection and that the immune response seen was mainly directed against a lower molecular weight product.

The results of the second immunization experiment are shown in the following table II.

TABLE II

| INOCULM | RAT | LOG GEOMETRIC MEAN TITERS | | |
|---|---|---|---|---|
| | | 1 week after 3rd injection | 1 weeks after 4th injection | 3 weeks after 4th injection |
| IMV-polio | 1 | 9 | 10 | 11 |
| pH 5.0 | 2 | 6 | 8 | 8 |
| CFA | 3 | — | 3 | 3 |
| TMV-polio | 4 | 2 | 4 | 1 |
| pH 8.0 | 5 | 4 | 6 | 4 |
| CFA | 6 | — | dead | dead |
| TMV-polio | 7 | 7 | 4 | 9 |
| RNA assembled | 8 | — | 1 | 6 |
| CFA | 9 | 2 | 5 | 5 |

The results of the above Table II show that the response to the pH 5.0 aggregated TMV-polio 3 was most similar to the RNA assembled response. The pH 5.0 product seems to induce a slightly higher level of immunity which indicated that the pH 5.0 aggregated TMV-polio 3 was not dissaggregating soon after injection. As expected, the immune response to the pH 8.0 dissaggregated product was lower confirming the importance of maintaining a high molecular weight for efficient immune response induction The RNA assembled TMV-Polio 3 was known to be stable at physiological pH as judged by E.M. and chromatographic studies.

EXAMPLE 12

This Example shows the results of dissaggregation experiments.

In order to present evidence that the TMV-polio 3 product was not dissaggregating soon after injection into rats in the immunisation tests presented in Example 11, a sample of TMV-polio 3 aggregated at pH 5.0 was dialyzed into phosphate buffered saline at pH 7.0 at 37° C. and chromatographed on Sepharose 6B under the same conditions. The results showed that the product still migrated in the void peak indicating that dissaggregation had not occured. A similar sample of TMV-polio 3 at pH 5.0 was dialyzed into a pH 8.0 buffer at 0° C. and also chromatographed. This material was found exclusively in the inclusion fractions showing that dissaggregation had taken place. It follows from these results that dissaggregation of TMV-polio 3 occurs at alkaline pH in the cold but probably does not occur under physiological conditions.

EXAMPLE 13

This Example illustrates the formation of plasmid pTMV-Polio 1 and-its expression in cell cultures.

The Apa I-Bam HI fragment of pTMV-6 coding for the C-terminus of the TMV coat protein was removed and replaced with a restriction fragment coding for the coat protein C-terminus plus two glycines and a 12 amino acid epitope from the VP2 protein of polio type 1. The resulting plasmid pTMV-Polio 1 is illustrated in FIG. 5. When *E.coli* strain JM103 containing this modified plasmid was induced with IPTG there was produced a TMV-like product which aggregated at pH 5.0 and migrated with a mobility slightly slower that the TMV coat protein marker on SDS polyacrylamide gels. This product is referred to as TMV-polio 1.

EXAMPLE 14

This Example illustrates the coaggregation of TMV-Polio 1 and TMV-Polio 3.

Samples of TMV-polio 1 and TMV-polio 3 which were prepared following the procedures of Examples 7 and 13 respectively and purified at pH 5.0 were mixed together at pH 8.0 and allowed to copolymerize at pH 5.5. All pH changes were performed by dialysis. The copolymerization reaction was monitored by electron microscopy in which anti-Type 3 antibody was added and the sample examined for antibody binding. It was found that all rods observed under the electron microscope demonstrated significant antibody binding suggesting that all rods formed were composed of both the TMV-Polio 1 and TMV-Polio 3 types of subunit and that no rods were composed of only the TMV-Polio 1 sub-unit. Control samples consisting of either TMV-Polio 3 rods were also treated with anti-type 3 antibody and examined. It was found that the TMV-Polio 3 rods were significantly covered with antibody whereas the TMV-Polio 1 rods failed to react. (See FIGS. 11A.1, 11A.2, 11B.1, 11B.2, 11C.1 and 11C.2)

SUMMARY OF DISCLOSURE

In summary of this disclosure, the present invention provides unique protein conjugate products comprising a self-aggregated protein and a hapten, which aggregate to form multivalent immunogenic materials upon aggregation, suitable for use in a vaccine. Modifications are possible within the scope of this invention.

What we claim is:

1. A method of forming a proteinaceous material in the form of a polymerized aggregated conjugate protein, which comprises:

constructing a heterologous plasmid expression vector comprising a first nucleotide sequence coding for the coat protein of tobacco mosaic virus, a second nucleotide sequence coding for a peptide containing an epitope from a pathogen, wherein said first and second nucleotide sequences form an open reading frame, and a promoter operatively coupled to said reading frame to direct expression of a fusion protein encoded by said open reading frame, introducing the plasmid expression vector into *E. coli*, growing the *E. coli* containing the expression vector to express the fusion protein, separating the fusion protein from the *E. coli* to provide a solution of fusion protein, modifying the pH of the solution to a pH of 5.0 at which said fusion protein forms a polymerized aggregated conjugate protein of tobacco mosaic virus and at least one epitope, and isolating the polymerized aggregated conjugate protein.

* * * * *